(12) United States Patent
Sung et al.

(10) Patent No.: US 10,094,806 B2
(45) Date of Patent: Oct. 9, 2018

(54) METHOD AND APPARATUS FOR MONITORING BATTERY STATE

(71) Applicant: Samsung Electronics Co., Ltd., Suwon-si (KR)

(72) Inventors: Jaemo Sung, Hwaseong-si (KR); Jeonghyun Park, Seoul (KR); Taejung Yeo, Yongin-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 181 days.

(21) Appl. No.: 15/064,898

(22) Filed: Mar. 9, 2016

(65) Prior Publication Data

US 2017/0261473 A1 Sep. 14, 2017
US 2018/0106766 A9 Apr. 19, 2018

(30) Foreign Application Priority Data

Mar. 9, 2015 (KR) .......................... 10-2015-0032723

(51) Int. Cl.
*G01N 29/44* (2006.01)
*B60L 11/18* (2006.01)
*G01N 29/12* (2006.01)

(52) U.S. Cl.
CPC .......... *G01N 29/12* (2013.01); *B60L 11/1851* (2013.01); *G01N 29/4454* (2013.01)

(58) Field of Classification Search
CPC .. B60L 11/1851; G01N 29/4454; G01N 29/12
USPC ......................................................... 73/602
See application file for complete search history.

(56) References Cited

U.S. PATENT DOCUMENTS

| | | | | |
|---|---|---|---|---|
| 4,231,259 A * | 11/1980 | Thiruvengadam | ..... | G01N 29/11 73/584 |
| 5,410,406 A * | 4/1995 | Webster | ................ | G01B 9/021 356/35.5 |
| 6,119,064 A * | 9/2000 | Nakaguro | ............ | G01R 31/007 701/115 |
| 8,033,788 B2 * | 10/2011 | Egedal | .................. | F03D 7/0292 416/43 |
| 9,417,331 B2 * | 8/2016 | Valentino | .............. | G01J 1/0219 |
| 9,528,629 B2 * | 12/2016 | Anderson | .......... | G05B 23/0235 |
| 9,561,864 B2 * | 2/2017 | Conrad | .................. | B64D 45/00 |
| 2007/0229248 A1 * | 10/2007 | Mott | ........................ | G01H 1/16 340/522 |
| 2012/0003526 A1 | 1/2012 | Kume et al. | | |
| 2014/0077593 A1 | 3/2014 | Schaefer | | |

FOREIGN PATENT DOCUMENTS

| | | |
|---|---|---|
| JP | 2014-63737 A | 4/2014 |
| JP | 2014-122817 A | 7/2014 |
| KR | 10-2007-0077871 A | 7/2007 |
| KR | 10-2011-0064057 A | 6/2011 |
| KR | 10-2012-0037154 A | 4/2012 |

\* cited by examiner

*Primary Examiner* — J M Saint Surin
(74) *Attorney, Agent, or Firm* — NSIP Law

(57) ABSTRACT

A method and an apparatus for monitoring battery state are provided. A method of monitoring battery state involves collecting vibration information based on a signal from an acceleration sensor, calculating a cumulative impact based on the vibration information, and estimating a degree of damage to a battery based on the cumulative impact.

23 Claims, 9 Drawing Sheets

100

110

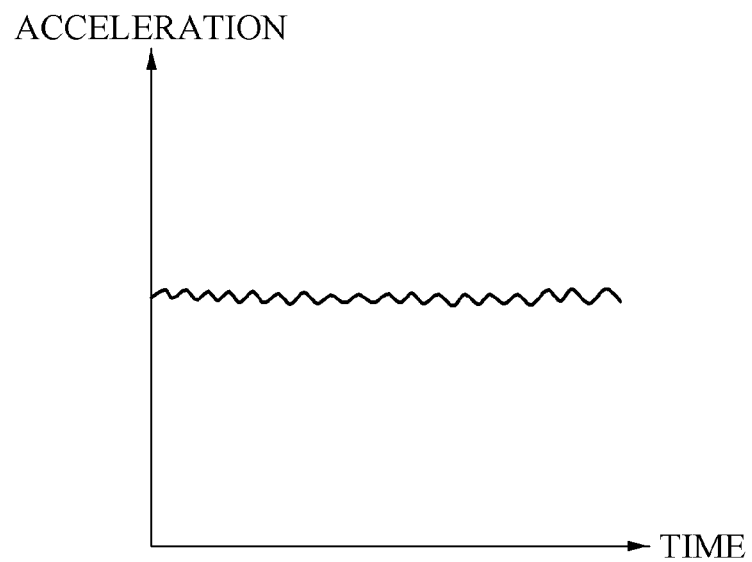

METHOD AND APPARATUS FOR MONITORING BATTERY STATE

CROSS-REFERENCE TO RELATED APPLICATION

This application claims the benefit under 35 USC 119(a) of Korean Patent Application No. 10-2015-0032723 filed on Mar. 9, 2015, in the Korean Intellectual Property Office, the entire disclosure of which is incorporated herein by reference for all purposes.

BACKGROUND

1. Field

The following description relates to a method and an apparatus for monitoring battery state based on an acceleration sensor signal received from an acceleration sensor.

2. Description of Related Art

With the recent increase in demand for electric and hybrid vehicles, researches are underway to develop a battery technology that may serve as a core power-supplying element of electric vehicles or hybrid vehicles. As a result, chargeable high-power secondary batteries have been developed for use in electric and hybrid vehicles. For example, lithium-ion batteries may be used as core power-supplying components of electric vehicles due to their high energy density.

A secondary battery includes a cathode active material, an anode active material, a separation membrane for separating the active materials, an electrolyte, and terminals connecting an electrode assembly and connected through a lead tab. A lithium ion may move along portions connected through the lead tab.

However, a connecting portion that connects the electronic assembly to the lead tab may be damaged due to external vibrations or physical impacts that may occur to the battery. When the battery is poorly connected to the electronic assembly due to the deterioration of the connecting portion, a performance of the secondary battery may correspondingly deteriorate, and the connecting portion may act as a resistor to generate heat. The heat generated from the connecting portion may diffuse into the secondary battery and may increase an internal temperature of the battery, decomposing the separation membrane and the electrolyte disposed therein. Due to the thermal runaway of the battery, an explosion or a fire may occur. In the event such a thermal runaway occurs in a battery for an electric vehicle while the electric vehicle is on a road, a traffic accident inviting vast human and physical damage may result.

Research has been conducted on a vibration reducing device to reduce a risk of vibrations in a high-capacity battery system for an electric vehicle. However, such a device may be used to only prevent an accident by estimating a degree of degradation of a battery due to the vibrations or by estimating the length of time it will take the battery to breakdown or get exhausted. Based on the current design of electric vehicles, batteries are constantly subjected to vibrations based on road conditions or other environmental factors. Further, batteries may be subjected to a great impact due to a situation encountered by an electric vehicle, such as a car accident. However, increasing the performance of such a protective device in order to eliminate or reduce impacts imposed on batteries while electric vehicles are driven may be difficult and may substantially increase the production cost of electric vehicles.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a method of monitoring battery state, the method involving collecting vibration information based on a signal from an acceleration sensor, calculating a cumulative impact based on the vibration information, and estimating a degree of damage to a battery based on the cumulative impact.

The collecting of the vibration information may involve monitoring the signal from the acceleration sensor, extracting an acceleration sensor signal block for a predetermined period of time in response to an amplitude of the signal being greater than or equal to a predetermined first threshold value, determining a frequency and an impact magnitude level of the acceleration sensor signal block, and generating an impact profile based on the impact magnitude level and a number of events corresponding to a frequency band including the determined frequency.

The determining of the frequency and the impact magnitude level of the acceleration sensor signal block may involve converting the acceleration sensor signal block to a frequency domain, selecting, from the frequency domain, a main impact response frequency at which a frequency response coefficient exceeds a predetermined second threshold value, and determining the main impact response frequency to be the frequency of the acceleration sensor signal block.

The determining of the frequency and the impact magnitude level of the acceleration sensor signal block may involve calculating an average acceleration amplitude of the acceleration sensor signal block, and selecting an impact magnitude level among a plurality of impact magnitude levels based on the average acceleration amplitude.

The calculating of the cumulative impact may involve calculating the cumulative impact based on the impact profile generated using the vibration information and based on a weighting profile.

The weighting profile may be generated based on a frequency weighting profile indicating a degree of influence of a frequency band on the degree of damage, and an impact magnitude weighting profile indicating a degree of influence of an impact magnitude level on the degree of damage.

The calculating of the cumulative impact may involve calculating the cumulative impact by calculating an element-wise product between a matrix of the weighting profile and a matrix of the impact profile.

The estimating of the degree of damage may involve estimating a total magnitude of damage due to impacts using the cumulative impact.

The general aspect of the method may further involve measuring a degree of similarity between a pattern of reference sensing data obtained by sensing at least one of a voltage, a current, and a temperature of a normal battery and a pattern of target sensing data obtained by sensing at least one of a voltage, a current, and a temperature of a target battery; and estimating a state of the target battery using the estimated degree of damage and the measured degree of similarity.

The estimating of the state of the target battery using the degree of damage and the degree of similarity may involve determining the target battery to be in an error state in response the degree of similarity being less than a predetermined value, and determining a contact fault as a cause of the error state based on the estimated degree of damage.

The estimating of the contact fault may be performed using at least one machine learning classification model among a neural network, a support vector machine, and a decision tree model.

In another general aspect, an apparatus for monitoring battery state includes a collector configured to collect vibration information based on a signal from an acceleration sensor, an impact calculator configured to calculate a cumulative impact based on the vibration information, and a damage estimator configured to estimate a degree of damage to the battery based on the cumulative impact.

The collector includes a monitorer configured to monitor the signal, a block extractor configured to extract an acceleration sensor signal block for a predetermined period of time in response to an amplitude of the acceleration sensor signal being greater than or equal to a predetermined first threshold value, a determiner configured to determine a frequency and an impact magnitude level of the acceleration sensor signal block, and a profile generator configured to generate an impact profile based on the impact magnitude level and a number of events corresponding to a frequency band including the determined frequency.

The determiner may be configured to convert the acceleration sensor signal block to a frequency domain; select, from the frequency domain, a main impact response frequency at which a frequency response coefficient exceeds a predetermined second threshold value; and determine the main impact response frequency to be the frequency of the acceleration sensor signal block.

The determiner may be configured to calculate an average acceleration amplitude of the acceleration sensor signal block and select an impact magnitude level among a plurality of impact magnitude levels based on the average acceleration amplitude.

The impact calculator may be configured to calculate the cumulative impact based on the impact profile generated using the vibration information and based on a weighting profile.

The weighting profile may be generated based on a frequency weighting profile indicating a degree of influence of a frequency band on the degree of damage and an impact magnitude weighting profile indicating a degree of influence of an impact magnitude level on the degree of damage.

The damage estimator may be configured to estimate a total magnitude of damage due to impacts using the cumulative impact.

The general aspect of the apparatus may further include a similarity measurer configured to measure a degree of similarity between a pattern of reference sensing data obtained by sensing at least one of a voltage, a current, and a temperature of a normal battery and a pattern of target sensing data obtained by sensing at least one of a voltage, a current, and a temperature of a target battery; and a state estimator configured to determine a state of the target battery using the estimated degree of damage and the measured degree of similarity.

The state estimator may be configured to determine the target battery to be in an error state in response to the degree of similarity being less than a predetermined value, and determine a contact fault as a cause of the error state based on the estimated degree of damage.

In another general aspect, an apparatus for monitoring battery state includes a processor configured to process a signal received from an acceleration sensor to determine an impact magnitude level for an impact event based on threshold values stored in a memory, generate an impact profile based on the determined impact magnitude level, calculate a cumulative impact based on the impact profile, and estimate a degree of damage to the battery based on the cumulative impact.

The processor may be configured to determine the impact magnitude level for the impact event by monitoring the signal received from the acceleration sensor, extracting an acceleration sensor signal block in response to an amplitude of the signal being greater than or equal to a predetermined first threshold value, and determining the impact magnitude level of the acceleration sensor signal block based on an average amplitude of the signal from the acceleration sensor signal block.

The processor may be included in a chip configured to be mounted to an electronic control unit.

Other features and aspects will be apparent from the following detailed description, the drawings, and the claims.

BRIEF DESCRIPTION OF THE DRAWINGS

FIGS. 2A and 2B are graphs illustrating examples of acceleration sensor signals generated in response to impacts received by a battery.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1A:
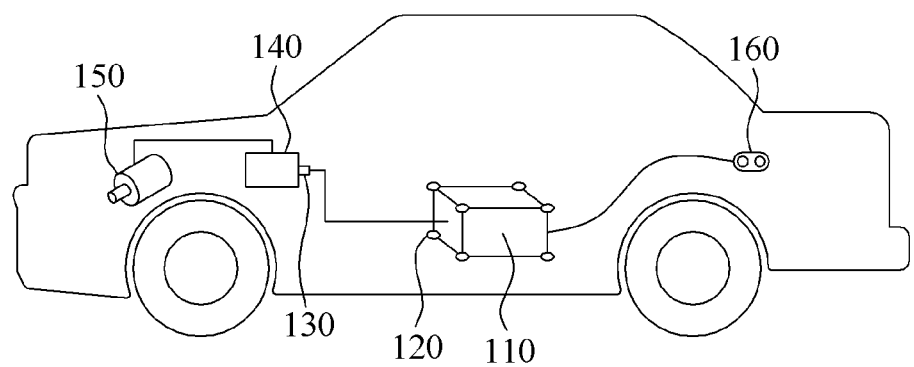
FIG. 1A is a diagram illustrating an example of an apparatus for monitoring battery state installed in a vehicle.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations is described as an example; the sequence of operations is not limited to that set forth herein and may be changed as is known in the art, with the exception of steps and/or operations that necessarily occur in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure is thorough, complete, and conveys the full scope of the disclosure to one of ordinary skill in the art.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "include" and/or "have," when used in this disclosure, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which this disclosure belongs.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

FIG. 1A is a diagram illustrating an example of an application of an apparatus for monitoring battery state. Hereinafter, the apparatus for monitoring battery state will be referred to as a battery state monitoring apparatus for simplicity.

Referring to FIG. 1A, the battery state monitoring apparatus 130 is applied to an electric vehicle 100. In this example, the battery state monitoring apparatus 130 may detect, in real time, whether a battery 110 is broken or damaged based on a degree of damage due to an impact as estimated by the battery state monitoring apparatus 130. In addition, the battery state monitoring apparatus 130 may further estimate a state of the battery 110 based on estimated influence of a vibrating impact on a state of charge (SoC), a state of health (SoH), and a useful remaining life of the battery 110. As illustrated in FIG. 1A, to more accurately measure a degree of physical impact on the battery 110, one or more acceleration sensors 120 may be directly attached to the battery 110. In this example, the acceleration sensors 120 are attached to corners of the battery 110. Thus, a degree of sensitivity and a location of the impact may be measured by the acceleration sensors 120. In this example, a plurality of acceleration sensors 120 are provided to detect the acceleration. However, the present disclosure is not limited thereto.

The battery state monitoring apparatus may be provided in a form of a chip to be directly mounted to an electronic control unit (ECU) 140. In this example, the battery state monitoring apparatus 130 is mounted on the ECU 140. However, in another example, the battery state monitoring apparatus 130 may be separately provided in a form configured to communicate with the ECU 140.

In this example, the battery 110 is a rechargeable battery connected to a power charging port 160 via a charger that regulates the charging process of the battery 110. The signals from the acceleration sensors 120 may be transmitted to the battery state monitoring apparatus 130 via hardwire connections. Further, the battery 110 provides electric power to the electric motor 150 via power cables. The ECU 140 regulates the electric motor 150 and the power output from the battery 110.

While an electric vehicle is illustrated in FIG. 1A, the battery state monitoring apparatus 130 may be applied to other types of vehicles. For example, in a hybrid vehicle, the vehicle may further include a combustion engine and a gas tank, and the battery may be connected to the combustion engine via a power resource managing unit. The battery state monitoring apparatus 130 may be mounted on the power resource managing unit, on the battery, or at another location, and configured to communicate with the power resource managing unit.

In another example of an electric vehicle, the battery state monitoring apparatus 130 may be applied to a battery management system (BMS).

In yet another example, the battery state monitoring apparatus 130 may be applied to an electronic device or an electronic management system that uses a rechargeable battery.

The battery state monitoring apparatus 130 may be widely applied to monitor battery state of a battery by providing additional information to an existing device used for diagnosing the battery state.

Also, the battery state monitoring apparatus 130 may be expansively applied to various other electronic devices that uses a battery. For example, the battery state monitoring apparatus 130 may be applied to a smartphone and a wearable device.

Figure 1B:
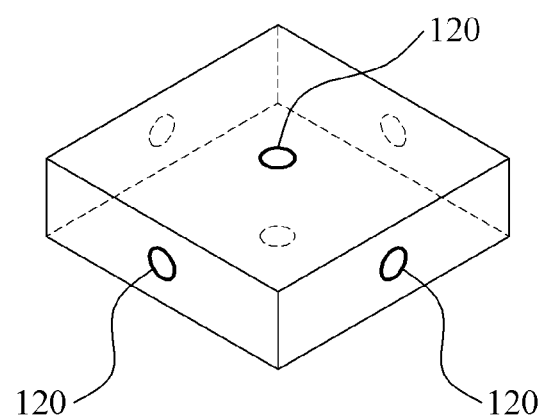
FIG. 1B is a diagram illustrating an example of an arrangement of sensors on a battery according to one example of an apparatus for monitoring battery state.
Figure 1C:
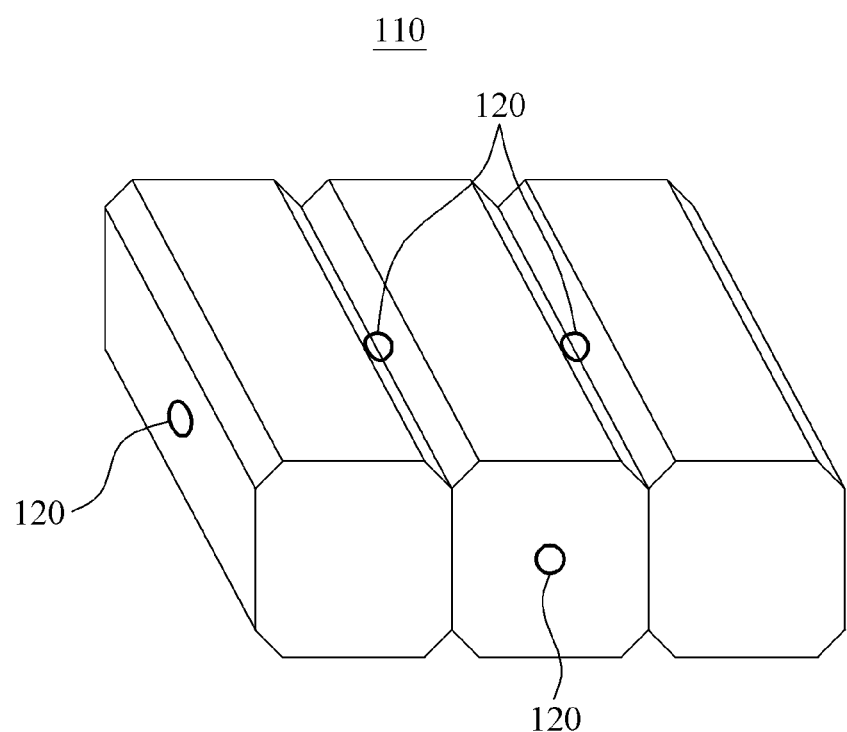
FIG. 1C is a diagram illustrating another example of an arrangement of sensors on a battery according to another example of an apparatus for monitoring battery state.

FIGS. 1B and 1C illustrate examples of sensor arrangements according to additional examples of apparatuses for monitoring battery state.

Rather than placing the acceleration sensors 120 around the corners of a battery 110 as illustrated in FIG. 1A, in FIG. 1B, the acceleration sensors 120 are placed at the center of each outer surface of the battery 110. In this examples, the battery 110 may be a battery pack that includes two or more energy storing modules within the battery 110.

FIG. 1C illustrates another example in which some of the acceleration sensors 120 are positioned between separate battery units that make up the battery 110. Various other arrangements of acceleration sensors 120 are possible with the battery 110.

Figure 2B:
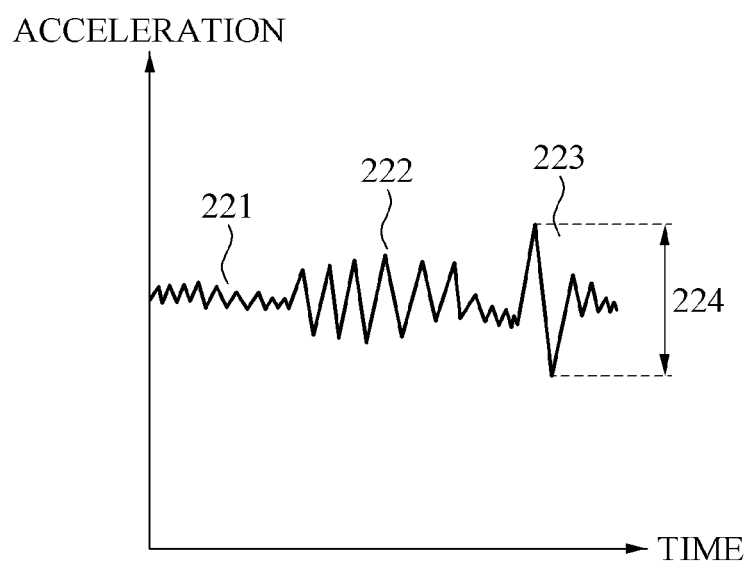

FIGS. 2A and 2B illustrate graphs of acceleration sensor signals generated in response to impacts received by a battery.

Referring to FIGS. 2A and 2B, graph 210 and graph 220 illustrate examples of acceleration sensor signal patterns generated due to vibrations that may occur in an electric vehicle or a hybrid vehicle.

Graph 210 of FIG. 2A illustrates an acceleration sensor signal generated during a static state of an electric vehicle or a hybrid vehicle. Referring to FIG. 2A, the impacts generated from microvibrations may not affect the battery state or only have an insignificant influence on the battery state.

Graph 220 of FIG. 2B illustrates an acceleration sensor signal that may occur while the vehicle is moving. For example, in a state 221, the vehicle is traveling on a paved road, and an acceleration sensor signal may not have a large amplitude. In a state 222, the vehicle is traveling on an unpaved road, and an amplitude of the acceleration sensor signal may be greater in comparison to when the vehicle is traveling on a paved road. In a state 223, the vehicle is traveling on a bumpy road, and the amplitude 224 of the acceleration sensor signal may be much greater than when the vehicle is traveling on an unpaved road or paved road. The acceleration sensor signal may change due to a type of an impact and a magnitude of an impact. For another example, in a case of a smartphone being dropped on a floor, an amplitude of an acceleration sensor signal may greatly increase for a short period of time. For still another example, in a case that a user exercises while wearing a wearable device, an amplitude of an acceleration sensor signal may increase.

Figure 3:
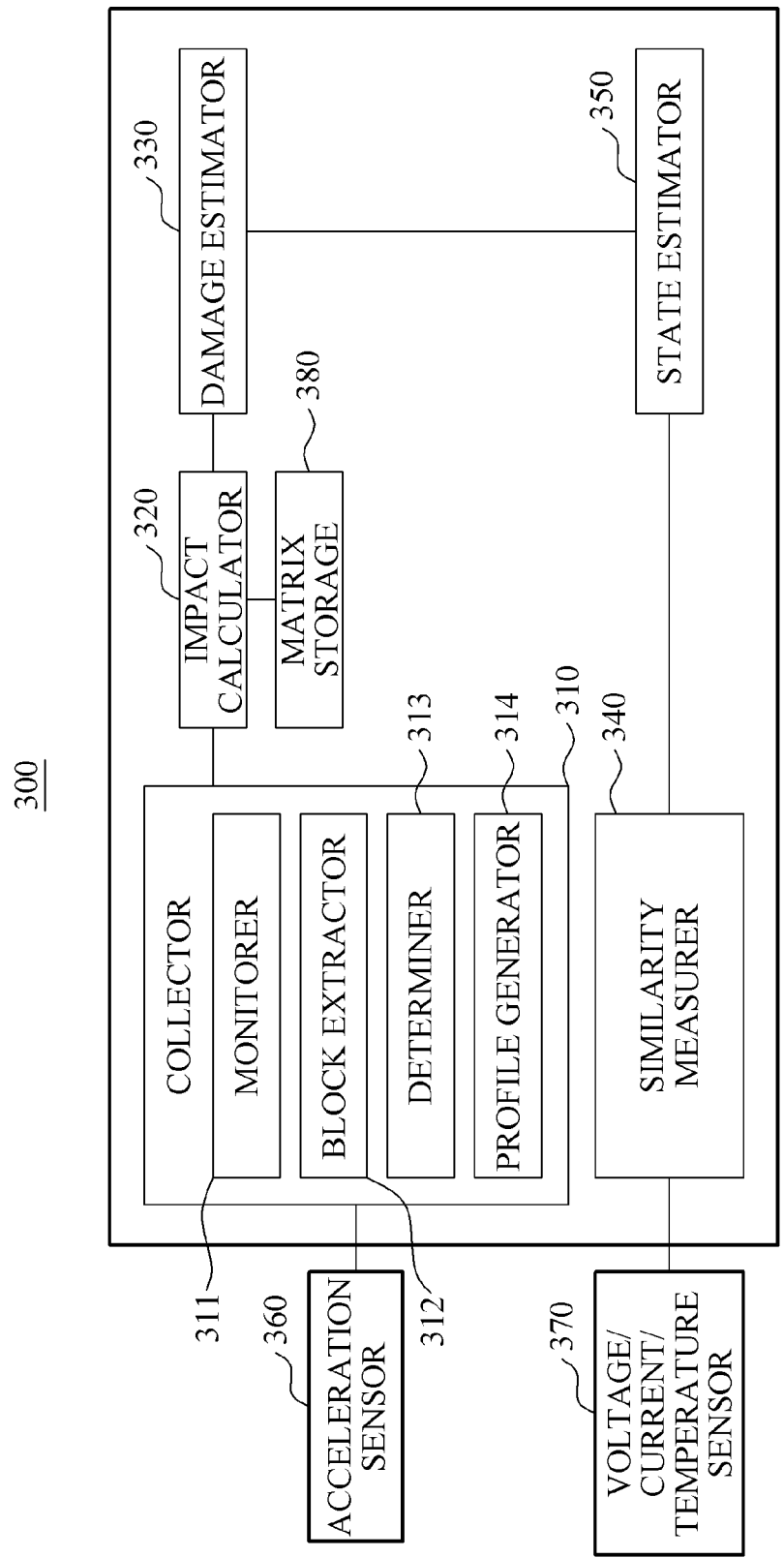
FIG. 3 is a diagram illustrating an example of an apparatus for monitoring battery state.

FIG. 3 is a diagram illustrating an example of a battery state monitoring apparatus 300.

Referring to FIG. 3, the battery state monitoring apparatus 300 includes a collector 310, an impact calculator 320, and a damage estimator 330. The collector 310, the impact calculator 320, and the damage estimator 330 may be implemented with one or more processors, signal processors and/or memories.

The collector 310 processes an acceleration sensor signal measured by an acceleration sensor 360 and collects vibration information from the acceleration sensor signal.

The battery state monitoring apparatus 300 detects a contact fault in connected portions of a battery using the collected vibration information. For example, when the contact fault occurs in a connected portion of the battery, a function of the battery may deteriorate due to a decrease in electric power and an increase in resistance. Such a contact fault occurring in a battery while the electric vehicle is traveling may lead to a severe accident. The battery state monitoring apparatus 300 may be applied to a battery fault detection device to enable a more accurate diagnosis of a fault.

The collector 310 includes a monitorer 311, a block extractor 312, a determiner 313, and a profile generator 314.

The monitorer 311 monitors an acceleration sensor signal of the acceleration sensor 360.

The acceleration sensor 360 may be attached directly to a target battery for which damage estimation is to be performed. The acceleration sensor 360 periodically measures information on acceleration in a tri-axial direction. The monitorer 311 continuously monitors the amplitude of an acceleration sensor signal that is continuously transmitted from the acceleration sensor 360.

The acceleration sensor 360 generates three-dimensional (3D) acceleration sensor signal. The generated acceleration sensor signal may include a time stamp recording a sensing time.

The block extractor 312 extracts an acceleration sensor signal block for a predetermined period of time, in response to the amplitude of the acceleration sensor signal being greater than or equal to a predetermined first threshold value.

The first threshold value indicates an acceleration value that may influence damage to a battery, and may be experimentally obtained. For example, while an electric vehicle is on ignition with a running engine without moving, microvibrations may be generated. In such an example, an acceleration sensor signal that does not have influence on a contact fault of a battery of the vehicle may be detected. For another example, when a user wearing a wearable device performs a walking motion, microvibrations may be generated. In such an example, an acceleration sensor signal that does not have influence on a contact fault of a battery of the device may be detected. In this example, in response to a determination that the amplitude of the acceleration sensor signal is less than the first threshold value, the amplitude of the acceleration sensor signal is considered to be an impact insufficient to influence an actual damage to the battery.

The amplitude of the acceleration sensor signal may be a maximum absolute value of a 3D acceleration sensor signal. The amplitude of the acceleration sensor signal may be defined as a norm of a tri-axial acceleration vector.

The determiner 313 determines a frequency and an impact magnitude level of the acceleration sensor signal block.

The determiner 313 quantifies the acceleration sensor signal collected from the acceleration sensor 360 measuring acceleration of the battery.

The determiner 313 converts the acceleration sensor signal block to a frequency domain, and selects, from the frequency domain, a main impact response frequency at which a frequency response coefficient exceeds a predetermined second threshold value, and determines the main impact response frequency to be the frequency of the acceleration sensor signal block.

The determiner 313 converts the acceleration sensor signal block to the frequency domain to measure a frequency. The determiner 313 selects, from the frequency domain, the main impact response frequency at which the frequency response coefficient exceeds the second threshold value. The determiner 313 determines the main impact response frequency to be the frequency of the acceleration sensor signal block.

In an example, a fast Fourier transform (FFT) may be performed on the acceleration sensor signal block to convert the acceleration sensor signal block expressed in a time domain to the frequency domain. A comparison of the frequency response coefficient and the second threshold value may be performed to select a set of main impact response frequencies.

The determiner 313 calculates an average acceleration amplitude of the acceleration sensor signal block by averaging the amplitude of acceleration sensor signal from the acceleration sensor signal block, and selects an impact magnitude level corresponding to the average acceleration amplitude among pre-thresholded impact magnitude levels.

The determiner 313 determines the impact magnitude level of the acceleration sensor signal block in accordance with a predetermined standard. The determiner 313 calculates the average acceleration amplitude of the acceleration sensor signal block, and determines the impact magnitude level corresponding to the average acceleration amplitude. The impact magnitude level may be a level classified through thresholding based on an amplitude of an impact. For example, the impact magnitude level may be classified into three levels, for example, a high, a middle, and a low level. Although the impact magnitude level is classified into the three levels, for example, the high, the middle, and the low level, herein, the impact magnitude level may be classified into a greater number of levels or two levels.

The determiner 313 calculates the average acceleration amplitude of the acceleration sensor signal block and store the average acceleration amplitude in a memory. By comparing the calculated average acceleration amplitude with predetermined threshold values stored in a memory, the determiner 313 determine to which one of the pre-classified impact magnitude levels an intensity of an impact belongs.

The profile generator 314 generates an impact profile recording a number of events corresponding to a frequency band to which the frequency of the acceleration sensor signal block belongs and the impact magnitude level of the acceleration sensor signal block.

The profile generator 314 stores the generated impact profile in a memory and updates the stored impact profile that is quantified based on a cumulative number of events at an impact magnitude level at each frequency band, using the determined frequency and the impact magnitude level of the acceleration sensor signal block.

Table 1 illustrates an example of an impact profile matrix.

TABLE 1

| | | Frequency | | | | | | |
|---|---|---|---|---|---|---|---|---|
| | | 5 Hz | 10 Hz | 15 Hz | ... | ... | 50 Hz | 55 Hz | 60 Hz |
| Impact magnitude level | High | 5 | 10 | 3 | | | 1 | 2 | 0 |
| | Middle | 12 | 30 | 8 | | | 1 | 0 | 0 |
| | Low | 20 | 8 | 7 | | | 0 | 0 | 0 |

Referring to Table 1, a cumulative number of events occurring at each frequency band and each impact magnitude level is input to the impact profile matrix. The profile generator 314 extracts, in real time, an acceleration sensor signal block of an acceleration sensor signal exceeding the first threshold value, and updates, in real time, the impact profile based on a frequency band and an impact magnitude level of the extracted acceleration sensor signal block. The unit used in Table 1 is the number of events that took place.

The impact calculator 320 calculates a cumulative impact based on the vibration information.

The impact calculator 320 calculates the cumulative impact based on the impact profile generated using the vibration information and on a weighting profile. The impact calculator 320 stores the calculated cumulative impact value in a memory.

The weighting profile may be generated based on a frequency weighting profile indicating a degree of influence of a frequency band on damage to the battery, and an impact magnitude weighting profile indicating a degree of influence of an impact magnitude level on damage to the battery.

In this example, a weighted value includes a first weighted value indicating the degree of influence of a frequency band on damage to the battery, and a second weighted value indicating the degree of influence of an impact magnitude level on damage to the battery.

The impact calculator 320 calculates the cumulative impact by applying the weighting profile to the impact profile. The impact calculator 320 quantifies the cumulative impact by applying, to the impact profile generated by the profile generator 314, the weighting profile indicating the degree of influence on damage to the battery.

The impact calculator 320 calculates the cumulative impact by calculating an element-wise product of an impact profile matrix and a weighting profile matrix generated using the first weighted value and the second weighted value. Table 2 illustrates an example of a weighting profile matrix.

TABLE 2

| | | Frequency | | | | | | |
|---|---|---|---|---|---|---|---|---|
| | | 5 Hz | 10 Hz | 15 Hz | ... ... | 50 Hz | 55 Hz | 60 Hz |
| Impact magnitude level | High | 0.012 | 0.015 | 0.018 | | 0.03 | 0.03 | 0.03 |
| | Middle | 0.006 | 0.0075 | 0.009 | | 0.015 | 0.015 | 0.015 |
| | Low | 0.002 | 0.0025 | 0.003 | | 0.005 | 0.005 | 0.005 |

Referring to Table 2, the weighting profile matrix including weighting information based on a frequency and an impact magnitude level is illustrated. Elements of the weighting profile matrix may indicate the degrees of influence of a frequency and an impact magnitude level on damage to the battery. The weighting profile matrix is normalized; thus, a sum of the elements becomes 1. In this example, a higher weighted value may indicate a higher risk of damage to the battery. Such a weighting profile matrix may be experimentally obtained and stored in advance in a matrix storage 380. In this example, the matrix storage 380 is a memory storage having a hardware component. The weighting profile matrix may be generated by experimentally calculating a difference or a ratio between a value obtained by determining a degree of deterioration of a battery when an impact is applied at a corresponding frequency and a corresponding impact magnitude level, and a value obtained by measuring deterioration of the battery when the battery normally operates. According to one example, the measuring of the deterioration of the battery may involve using a value used to measure information on a level of damage including deterioration of a capacity of the battery or an increase in impedance.

The calculating of the element-wise product of the weighting profile matrix and the impact profile matrix may indicate multiplying values placed at corresponding locations in each matrix. A total magnitude of damage may be a sum of element-wise products.

In this example, a considerable experimental cost may be used to obtain a weighted value using both a frequency and an impact magnitude level to generate the weighting profile matrix. Thus, a weighted value may be calculated by separately using a frequency and an impact magnitude level. Table 3 illustrates an example of a weighted damage value based on a frequency. Table 4 illustrates an example of a weighted damage value based on an impact magnitude level.

TABLE 3

| | | Frequency | | | | |
|---|---|---|---|---|---|---|
| 5 Hz | 10 Hz | 15 Hz | ... ... | 50 Hz | 55 Hz | 60 Hz |
| 0.02 | 0.02 | 0.03 | | 0.05 | 0.05 | 0.05 |

Referring to Table 3, a frequency weighting profile matrix including weighted value information based on a frequency is illustrated. Elements of the frequency weighting profile matrix indicate a degree of influence of a frequency on damage to a battery. The frequency weighting profile matrix is normalized; thus, a sum of the elements becomes 1. In this example, a higher weighted value indicates a higher probability that the battery is damaged; however, the present disclosure is not limited thereto. In another example, a lower weighted value may indicate a higher probability that the battery is damaged. Such a frequency weighting profile matrix may be experimentally obtained in advance and stored in the matrix storage 380.

TABLE 4

| Impact Magnitude Level | Weighted Value |
|---|---|
| Impact Magnitude Weighting Profile   High | 0.6 |
| Middle | 0.3 |
| Low | 0.1 |

Figure 4:
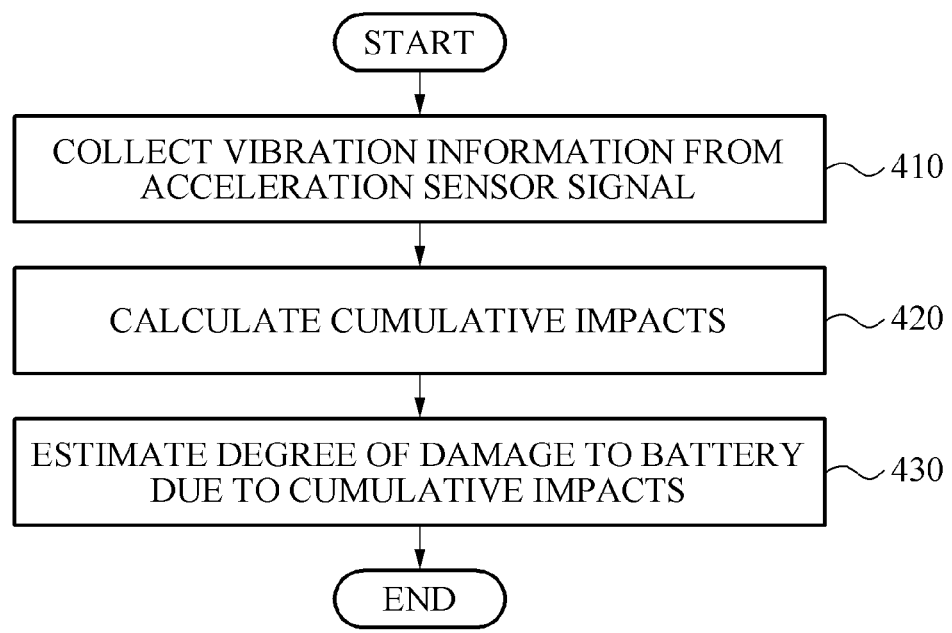
FIG. 4 is a flowchart illustrating an example of a method of monitoring battery state.

Referring to FIG. 4, an example of an impact magnitude weighting profile matrix including weighted value information based on an impact magnitude level is illustrated.

Elements of the impact magnitude weighting profile matrix indicate a degree of influence of an impact magnitude level on damage to a battery. The impact magnitude weighting profile matrix is normalized; thus, a sum of the elements becomes 1. In this example, a higher weighted value indicates a higher risk of damage; however, the present disclosure is not limited thereto. In another example, a lower weighted value may indicate a lower risk of damage. In yet another example, there may be two impact magnitude level or four or more impact magnitude level. Such an impact magnitude weighting profile matrix may be experimentally obtained in advance and stored in the matrix storage 380.

The weighting profile matrix of a frequency and an impact magnitude level, which is illustrated in Table 2, may be generated by calculating an outer product of the two matrices separately obtained based on a frequency and an impact magnitude level.

The damage estimator 330 estimates damage to the battery due to impacts based on the cumulative impact.

The damage estimator 330 estimates a total magnitude of damage due to impacts using the cumulative impact calculated by the impact calculator 320.

The battery state monitoring apparatus 300 further includes a similarity measurer 340 and a state estimator 350. The similarity measurer 340 and the state estimator 250 may be implemented with one or more processors, signal processors and/or memories.

The similarity measurer 340 determines a degree of similarity between a pattern of reference sensing data that is received from a voltage/current/temperature sensor 370 and obtained by measuring at least one of a voltage, a current, and a temperature of a normal battery, and a pattern of target sensing data that is obtained by measuring at least one of a voltage, a current, and a temperature of a target battery.

The voltage/current/temperature sensor 370 is a sensor configured to measure at least one of a voltage, a current, and a temperature of a battery. The voltage/current/temperature sensor 370 measures at least one of the voltage, the current, and the temperature of the target battery and the normal battery.

The similarity measurer 340 determines the degree of similarity between the pattern of the reference sensing data stored in a memory in advance and the pattern of the target sensing data. In an example, the similarity measurer 340 compares the pattern of the reference sensing data, which represents a pattern of an environment in which the normal battery is used, to the pattern of the target sensing data, which is measured in real time from the target battery, and determine the target battery to be in an abnormal state in response to a difference between the patterns exceeding a reference value.

The state estimator 350 estimates a state of the target battery based on the estimated damage and the measured degree of similarity.

In response to a determination that the degree of similarity measured by the similarity measurer 340 is less than a predetermined value, the state estimator 350 may estimate an error of the target battery. In this example, the state estimator 350 may detect a contact fault as a cause of the error based on the estimated damage.

For example, in the event that the target battery is detected to be in an error state by the similarity measurer 340 and it is determined that the damage is severe, the state estimator 350 may determine that the contact fault is the cause of the error. Although a failure in the battery may be detected through the measuring of a degree of similarity, whether a cause of the failure is a contact fault or an internal deterioration may not be easily verified. Thus, a failure in the battery caused by the contact fault may be determined using the damage estimated by the damage estimator 330 and accordingly, accuracy in detecting a cause of a failure in the battery may be improved.

The estimating of the contact fault may be performed by applying at least one machine learning classification model among a neural network, a support vector machine, and a decision tree model.

FIG. 4 is a flowchart illustrating an example of a method of monitoring battery state. The method to be described hereinafter may be performed by a processor of a BMS.

Referring to FIG. 4, in operation 410, a battery state monitoring apparatus collects vibration information from an acceleration sensor signal. An acceleration sensor may be attached directly to a target battery for which damage estimation is to be performed. The acceleration sensor may periodically measure acceleration information in a tri-axial direction.

The battery state monitoring apparatus detects a contact fault in a connected portion of the battery using the collected vibration information. A more accurate diagnosis of a failure in the battery may be enabled by applying the battery state monitoring apparatus to a battery failure detection device.

In operation 420, the battery state monitoring apparatus calculates a cumulative impact.

The battery state monitoring apparatus calculates the cumulative impact based on an impact profile generated using the vibration information and a weighting profile.

The weighting profile may be generated based on a frequency weighting profile indicating a degree of influence of a frequency band on damage to the battery and on an impact magnitude weighting profile indicating a degree of influence of an impact magnitude level on damage to the battery.

For example, a predetermined weighted value may be applied to the impact profile. The weighted value may include a first weighted value indicating the degree of influence of a frequency band on damage to the battery, and a second weighted value indicating the degree of influence of an impact magnitude level on damage to the battery.

The battery state monitoring apparatus estimates total damage to the battery by calculating an element-wise product of an impact profile matrix and a weighting profile matrix based on a frequency band and an impact magnitude level, which is generated using the first weighted value and the second weighted value.

The battery state monitoring apparatus calculates the cumulative impact by calculating an element-wise product between the weighting profile matrix and the impact profile matrix.

In operation 430, the battery state monitoring apparatus estimates a degree of damage to the battery due to impacts.

The battery state monitoring apparatus estimates a total magnitude of damage to the battery due to impacts using the cumulative impact.

Figure 5:
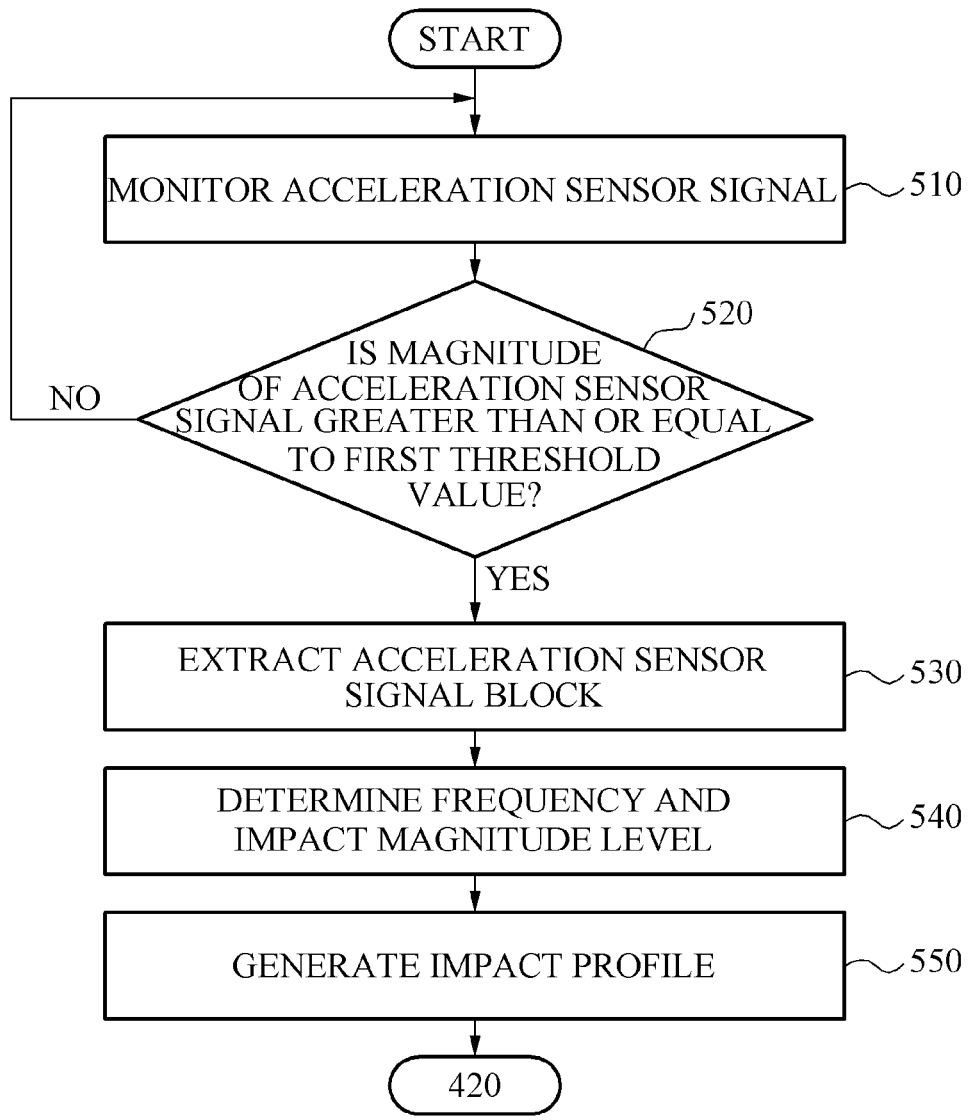
FIG. 5 is a flowchart illustrating a method of collecting vibration information according to an example of a method of monitoring battery state.

FIG. 5 is a flowchart illustrating an example of a method of collecting vibration information in a method of monitoring battery state.

Referring to FIG. 5, in operation 510, a battery state monitoring apparatus monitors an acceleration sensor signal.

According to one example of the battery state monitoring apparatus, an acceleration sensor is directly attached to a target battery for which damage estimation is to be performed. The acceleration sensor periodically measures acceleration information in a tri-axial direction, and generates a 3D acceleration sensor signal. The acceleration sensor signal may include a time stamp recording a sensing time.

In operation 520, the battery state monitoring apparatus determines whether an amplitude of the acceleration sensor signal is greater than or equal to a first threshold value.

The amplitude of the acceleration sensor signal may be a maximum absolute value of the 3D acceleration sensor signal. The amplitude of the acceleration sensor signal may be defined as a norm of a tri-axial acceleration vector.

In response to a determination that the amplitude of the acceleration sensor signal is greater than or equal to the first threshold value, operation 530 is performed. In response to a determination that the amplitude of the acceleration sensor signal is less than the first threshold value, operation 510 is performed. The first threshold value may be an acceleration value that may have influence on damage to the battery, and may be obtained in advance through experiments. In response to a determination that the amplitude of the acceleration sensor signal is less than the first threshold value, the amplitude may be considered to be an impact insufficient to influence actual damage to the battery.

In operation 530, the battery state monitoring apparatus extracts an acceleration sensor signal block.

The battery state monitoring apparatus extracts the acceleration sensor signal block for a predetermined period of time.

In operation 540, the battery state monitoring apparatus determines a frequency and an impact magnitude level of the acceleration sensor signal block.

The battery state monitoring apparatus quantifies the acceleration sensor signal collected from the acceleration sensor configured to measure acceleration of the battery.

In operation 550, the battery state monitoring apparatus generates an impact profile.

The battery state monitoring apparatus generates the impact profile recording a number of events corresponding to a frequency band to which the frequency of the acceleration sensor signal block belongs and the impact magnitude level of the acceleration sensor signal block.

Figure 6:
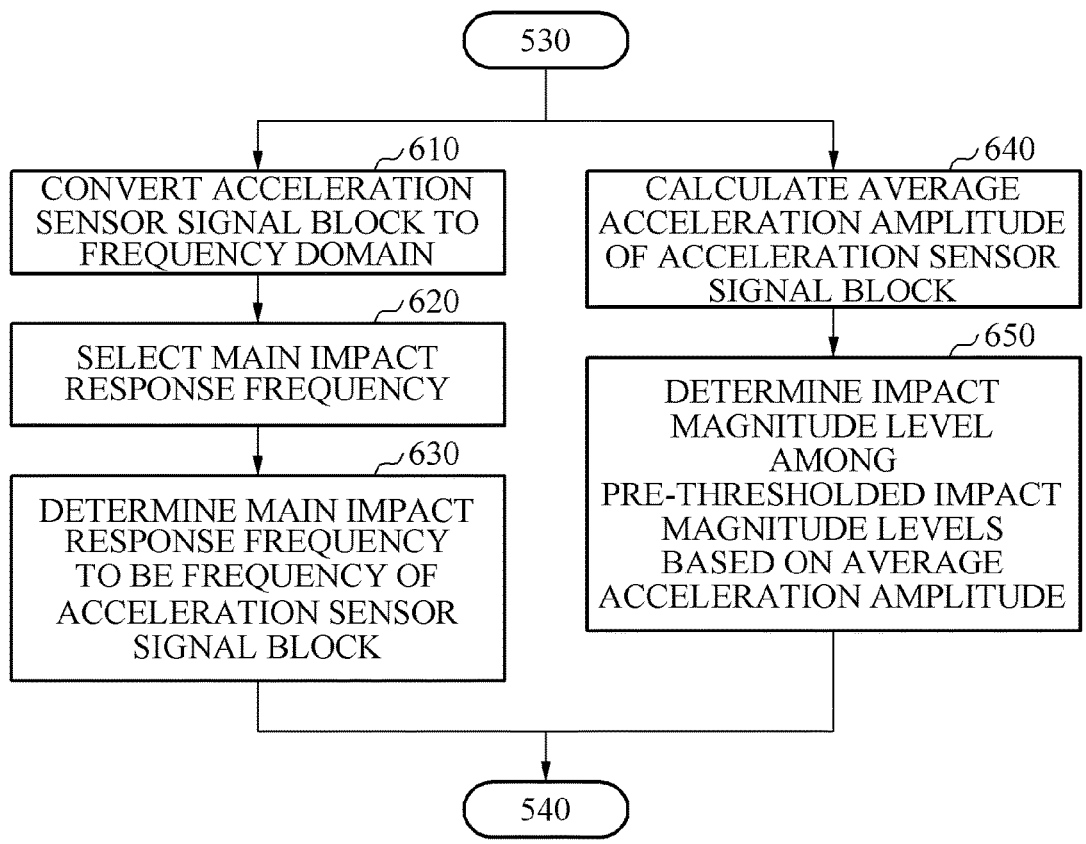
FIG. 6 is a flowchart illustrating a method of determining a frequency and an impact magnitude level according to an example of a method of collecting vibration information.

FIG. 6 is a flowchart illustrating an example of a method of determining a frequency and an impact magnitude level in a method of collecting vibration information.

Referring to FIG. 6, in operation 610, a battery state monitoring apparatus converts an acceleration sensor signal block to a frequency domain.

The battery state monitoring apparatus converts the acceleration sensor signal block expressed in a time domain to the frequency domain by performing a fast Fourier transformation on the acceleration sensor signal block.

In operation 620, the battery state monitoring apparatus selects a main impact response frequency.

The battery state monitoring apparatus selects, from the frequency domain, the main impact response frequency at which a frequency response coefficient exceeds a predetermined second threshold value. The battery state monitoring apparatus selects a set of main impact response frequencies by comparing, to the second threshold value, the frequency response coefficient of the acceleration sensor signal block in the frequency domain.

In operation 630, the battery state monitoring apparatus determines the main impact response frequency to be the frequency of the acceleration sensor signal block.

In operation 640, the battery state monitoring apparatus calculates an average acceleration amplitude of the acceleration sensor signal block.

The battery state monitoring apparatus determines the average acceleration amplitude of the acceleration sensor signal block to be an impact magnitude of the acceleration sensor signal block. Thus, the battery state monitoring apparatus determines, to be the impact magnitude level of the acceleration sensor signal block, an impact magnitude level to which the average acceleration amplitude of the acceleration sensor signal block belongs.

In operation 650, the battery state monitoring apparatus determines an impact magnitude level corresponding to the average acceleration amplitude among pre-thresholded impact magnitude levels based on the average acceleration amplitude of the acceleration sensor signal block.

The battery state monitoring apparatus determines the impact magnitude level of the acceleration sensor signal block in accordance with a predetermined standard. The battery state monitoring apparatus calculates the average acceleration amplitude of the acceleration sensor signal block, and determines the impact magnitude level corresponding to the average acceleration amplitude among the pre-thresholded impact magnitude levels. The impact magnitude level may refer to a level classified based on a magnitude of an impact through thresholding. For example, the impact magnitude level may be classified into three levels, such as a high level, a middle level and a low level. Although the impact magnitude level is classified into three levels in the example described herein, the impact magnitude level may be classified into a greater number of levels or two levels in another example.

The battery state monitoring apparatus calculates the average acceleration amplitude of the acceleration sensor signal block. Based on the calculated average acceleration amplitude, one of the classified impact magnitude levels to which an intensity of an impact belongs may be determined.

Figure 7:
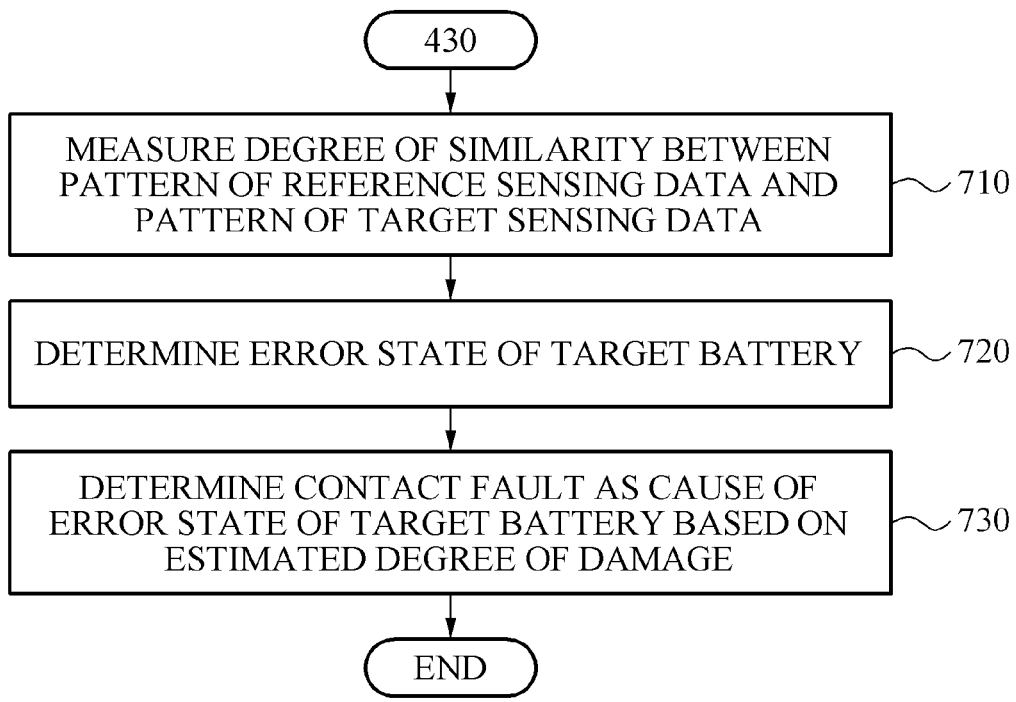
FIG. 7 is a flowchart illustrating a method of detecting a contact fault in a battery as a cause of an error state of the battery according to an example of a method of monitoring a state of the battery.

FIG. 7 is a flowchart illustrating a method of determining whether a contact fault is the cause of an error state of a battery according to another example of a method of monitoring battery state.

Referring to FIG. 7, in operation 710, a battery state monitoring apparatus measures a degree of similarity between a pattern of reference sensing data and a pattern of target sensing data.

The battery state monitoring apparatus measures the degree of similarity between the pattern of the reference sensing data obtained by sensing at least one of a voltage, a current, and a temperature of a normal battery, and the pattern of the target sensing data obtained by sensing at least one of a voltage, a current, and a temperature of a target battery.

The battery state monitoring apparatus estimates a state of the target battery using an estimated degree of damage and the measured degree of similarity.

In operation 720, the battery state monitoring apparatus determines that the target battery is in an error state.

For example, in response to a determination that a difference between the pattern of the reference sensing data and the pattern of the target sensing data exceeds a reference value, the target battery is determined to be in an error state.

In operation 730, the battery state monitoring apparatus determines a contact fault as a cause of the error state based on the estimated degree of damage.

b. In response to the target battery being in the error state and a magnitude of the estimated damage exceeding a reference value, the battery state monitoring apparatus determines the contact fault as the cause of the error state of the target battery. The contact fault may be detected based on the estimated degree of damage and the degree of similarity between the patterns.

The battery state monitoring apparatus may estimate the contact fault using at least one machine learning classification model among a neural network, a support vector machine, and a decision tree model.

A difference between patterns of a voltage, a current, and a temperature in a normal state and an error state of a battery of an electric vehicle may be generated not only by such a contact fault but also by the deterioration of an internal material of the battery or by various faults occurring within the battery. Thus, whether a contact fault or an internal error may have occurred cannot be easily detected based solely on analyzing a voltage/current/temperature sensor signal. When a battery error is caused by a contact fault, for example, a fault and a crack in a connected surface of a battery may be affected by an impact received when an electric vehicle travels. Thus, accuracy in monitoring the contact fault may be improved using an estimated degree of damage as input data to be input to a model for the contact fault.

The apparatuses, units, modules, devices, collectors, measurers, estimators, calculators and other components illustrated in FIGS. 1A-1C and 3 that perform the operations described herein with respect to FIGS. 4, 5, 6 and 7 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 4-7. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 4-7 may be performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of monitoring battery state, comprising:
  collecting vibration information associated with a target battery, based on signals from one or more acceleration sensors attached to the target battery;

calculating a cumulative impact based on the vibration information associated with the target battery; and estimating a degree of damage to the target battery based on the cumulative impact.

2. A method of monitoring battery state, comprising:
collecting vibration information based on a signal from an acceleration sensor;
calculating a cumulative impact based on the vibration information; and
estimating a degree of damage to a battery based on the cumulative impact, wherein the collecting of the vibration information further comprises:
monitoring the signal from the acceleration sensor;
extracting an acceleration sensor signal block for a predetermined period of time in response to an amplitude of the signal being greater than or equal to a predetermined first threshold value;
determining a frequency and an impact magnitude level of the acceleration sensor signal block; and
generating an impact profile based on the impact magnitude level and a number of events corresponding to a frequency band including the determined frequency.

3. The method of claim 2, wherein the determining of the frequency and the impact magnitude level of the acceleration sensor signal block comprises:
converting the acceleration sensor signal block to a frequency domain;
selecting, from the frequency domain, a main impact response frequency at which a frequency response coefficient exceeds a predetermined second threshold value; and
determining the main impact response frequency to be the frequency of the acceleration sensor signal block.

4. The method of claim 2, wherein the determining of the frequency and the impact magnitude level of the acceleration sensor signal block comprises:
calculating an average acceleration amplitude of the acceleration sensor signal block; and
selecting an impact magnitude level among a plurality of impact magnitude levels based on the average acceleration amplitude.

5. The method of claim 1, wherein the calculating of the cumulative impact comprises:
calculating the cumulative impact based on an impact profile generated using the vibration information and based on a weighting profile.

6. The method of claim 5, wherein the weighting profile is generated based on a frequency weighting profile indicating a degree of influence of a frequency band on the degree of damage, and an impact magnitude weighting profile indicating a degree of influence of an impact magnitude level on the degree of damage.

7. The method of claim 5, wherein the calculating of the cumulative impact comprises:
calculating the cumulative impact by calculating an element-wise product between a matrix of the weighting profile and a matrix of the impact profile.

8. The method of claim 1, wherein the estimating of the degree of damage comprises:
estimating a total magnitude of damage due to impacts using the cumulative impact.

9. A method of monitoring battery state, comprising:
collecting vibration information based on a signal from an acceleration sensor;
calculating a cumulative impact based on the vibration information;

estimating a degree of damage to a target battery based on the cumulative impact
measuring a degree of similarity between a pattern of reference sensing data obtained by sensing at least one of a voltage, a current, and a temperature of a normal battery and a pattern of target sensing data obtained by sensing at least one of a voltage, a current, and a temperature of the target battery; and
estimating a state of the target battery using the estimated degree of damage and the measured degree of similarity.

10. The method of claim 9, wherein the estimating of the state of the target battery using the degree of damage and the degree of similarity comprises:
determining the target battery to be in an error state in response to the degree of similarity being determined to be less than a predetermined value; and
determining a contact fault as a cause of the error state based on the estimated degree of damage.

11. The method of claim 10, wherein the estimating of the contact fault is performed using at least one machine learning classification model among a neural network, a support vector machine, and a decision tree model.

12. An apparatus for monitoring battery state, comprising:
a collector configured to collect vibration information associated with a target battery, based on signals from one or more acceleration sensors attached to the target battery;
an impact calculator configured to calculate a cumulative impact based on the vibration information associated with the target battery; and
a damage estimator configured to estimate a degree of damage to the target battery based on the cumulative impact.

13. The apparatus of claim 12, wherein the collector comprises:
a monitorer configured to monitor the signals;
a block extractor configured to extract an acceleration sensor signal block for a predetermined period of time in response to a corresponding amplitude of the acceleration sensor signals being greater than or equal to a predetermined first threshold value;
a determiner configured to determine a frequency and an impact magnitude level of the acceleration sensor signal block; and
a profile generator configured to generate an impact profile based on the impact magnitude level and a number of events corresponding to a frequency band including the determined frequency.

14. The apparatus of claim 13, wherein the determiner is configured to convert the acceleration sensor signal block to a frequency domain; select, from the frequency domain, a main impact response frequency at which a frequency response coefficient exceeds a predetermined second threshold value; and determine the main impact response frequency to be the frequency of the acceleration sensor signal block.

15. The apparatus of claim 13, wherein the determiner is configured to calculate an average acceleration amplitude of the acceleration sensor signal block and select an impact magnitude level among a plurality of impact magnitude levels based on the average acceleration amplitude.

16. The apparatus of claim 12, wherein the impact calculator is configured to calculate the cumulative impact based on an impact profile generated using the vibration information and based on a weighting profile.

17. The apparatus of claim 16, wherein the weighting profile is generated based on a frequency weighting profile indicating a degree of influence of a frequency band on the degree of damage and an impact magnitude weighting profile indicating a degree of influence of an impact magnitude level on the degree of damage.

18. The apparatus of claim 12, wherein the damage estimator is configured to estimate a total magnitude of damage due to impacts using the cumulative impact.

19. The apparatus of claim 12, further comprising:
a similarity measurer configured to measure a degree of similarity between a pattern of reference sensing data obtained by sensing at least one of a voltage, a current, and a temperature of a normal battery and a pattern of target sensing data obtained by sensing at least one of a voltage, a current, and a temperature of the target battery; and
a state estimator configured to determine a state of the target battery using the estimated degree of damage and the measured degree of similarity.

20. The apparatus of claim 19, wherein the state estimator is configured to determine the target battery to be in an error state in response to the degree of similarity being determined to be less than a predetermined value, and determine a contact fault as a cause of the error state based on the estimated degree of damage.

21. An apparatus for monitoring battery state, comprising:
a processor configured to:
process signals received from one or more acceleration sensors to determine an impact magnitude level for an impact event associated with a target battery, the one or more acceleration sensors being attached to the target battery;
calculate a cumulative impact based on the impact magnitude level associated with the target battery; and
estimate a degree of damage to the target battery based on the cumulative impact.

22. The apparatus of claim 21, wherein the processor is configured to determine the impact magnitude level for the impact event by monitoring the signals received from the one or more acceleration sensors, extracting an acceleration sensor signal block in response to a corresponding amplitude of the signals being greater than or equal to a predetermined first threshold value, and determining the impact magnitude level of the acceleration sensor signal block by processing the signals from the acceleration sensor signal block.

23. The apparatus of claim 21, wherein the processor is included in a chip configured to be mounted to an electronic control unit.

* * * * *